United States Patent
Brietzke et al.

(10) Patent No.: US 8,663,595 B2
(45) Date of Patent: Mar. 4, 2014

(54) PROCESS FOR PRODUCING AMMONIUM SALTS

(75) Inventors: Stephan Brietzke, Altendiez (DE); Peter Groer, Babenhausen (DE); Christoph Mollenkopf, Frankfurt am Main (DE); Michael J. Bayer, Eschborn (DE)

(73) Assignee: Celanese International Corporation, Dallas, TX (US)

( * ) Notice: Subject to any disclaimer, the term of this patent is extended or adjusted under 35 U.S.C. 154(b) by 279 days.

(21) Appl. No.: 13/333,047

(22) Filed: Dec. 21, 2011

(65) Prior Publication Data

US 2013/0164211 A1   Jun. 27, 2013

(51) Int. Cl.
*C01C 1/242*   (2006.01)
*C01C 1/24*   (2006.01)

(52) U.S. Cl.
USPC ............................. 423/549; 423/545

(58) Field of Classification Search
USPC ................................. 423/549, 545
See application file for complete search history.

(56) References Cited

U.S. PATENT DOCUMENTS 7,261,867 B1 *  8/2007  Sandford et al. ............ 423/45
2011/0256045 A1  10/2011  Brietzke et al.

FOREIGN PATENT DOCUMENTS

| CN | 1883790 | 12/2006 |
| DE | 3522470 | 1/1987 |
| DE | 35 45 196 A1 | 6/1987 |
| DE | 4416571 | 12/1995 |
| DE | 10146689 | 4/2003 |
| EP | 2 380 869 A1 | 10/2011 |
| EP | 2 380 870 A1 | 10/2011 |

OTHER PUBLICATIONS

International Search Report and Written Opinion mailed Apr. 17, 2013 in corresponding International Application No. PCT/US2012/069999.

* cited by examiner

*Primary Examiner* — Yong Chu

(57) ABSTRACT

In one embodiment, the invention is to a process for purifying a by-product stream. The process comprises the step of providing a by-product stream comprising an ammonium salt, dimerized amide, and optionally water. The process further comprises the step of precipitating at least a portion of the dimerized amide in the by-product stream to form solid dimerized amide. The process further comprises the step of separating the solid dimerized amide from the by-product stream to form a treated by-product stream comprising less than 1 wt. % solid dimerized amide.

20 Claims, 2 Drawing Sheets

PROCESS FOR PRODUCING AMMONIUM SALTS

FIELD OF INVENTION

The present invention relates generally to the production of ammonium salts. More specifically, the present invention relates to the production of a crude ammonium sulfate product and the separation thereof.

BACKGROUND OF THE INVENTION

Many conventional chemical processes yield process waste streams comprising acid, e.g., sulfuric acid, and amines, e.g., organic tertiary amines. The amines are commercially valuable and, as a consequence, it is desirable to recover the amines from the waste stream.

As one example of amine recovery, DE 101 46 689 discloses a method that utilizes distillation to recover organic amines from a catalyst waste stream that contains the amines and other impurities. As another example, DE 35 22 470 A discloses the use of a caustic soda to recover amines and metallic components from a polyphenylene ether synthesis waste stream. Also, DE 44 16 571 discloses the recovery of amines from an acidic stream. The process of DE 44 16 571 utilizes the addition of alkali bases to the acidic stream followed by distillation.

As another example, CN 1883790 describes the recovery of amines from a sulfuric acid/amine waste stream by neutralization with inorganic bases of oxide origin, e.g., NaOH, KOH, $Ca(OH)_2$, or $CaCO_3$. The neutralization of the sulfuric acid may, via side reactions, yield the respective sulfate, e.g. calcium sulfate or sodium sulfate. These sulfates may be disposed of or, if the sulfates are valuable, may be processed in order to obtain a useful and/or saleable end product. The processing, e.g., evaporation or drying, however, requires large amounts of energy. Also, due to the molar masses of the oxides that are required by the stoichiometry of these reactions, large quantities of oxides must be used. When calcium bases are employed, the calcium sulfate that is created precipitates during the reaction and, as such, the reaction suspension must either be diluted or thoroughly blended, which adds to the separation cost.

In other conventional processes, ammonia may be utilized as the inorganic base in the recovery of the amines. In such cases, the recovery process yields a recovered amine product stream and a by-product stream that comprises ammonium sulfate. The ammonium sulfate has commercial value, e.g., as a fertilizer, and may be collected and sold or otherwise utilized. Solids, however, are known to form in these conventional by-product streams. The solids cause processing and/or quality control problems. For example, the solids may collect on the walls of process equipment, e.g., tanks or pipes, which creates the need for costly maintenance. In some cases, the solids may form during transportation and/or storage, which results in a delivered product that is unacceptable to end users.

Even though conventional amine recovery processes may produce an ammonium sulfate by-product, the need remains for an improved process that yields an ammonium sulfate by-product that forms little or no solid formation over time.

All of the references discussed above are hereby incorporated by reference.

SUMMARY OF THE INVENTION

The present invention, in one embodiment, relates to a process for purifying a process stream from an ammonium salt production process, e.g., an ammonium salt-containing by-product stream. The (untreated) by-product stream comprises water, an ammonium salt, e.g., ammonium sulfate, and dimerized amide. The process further comprises the step of precipitating at least a portion of the dimerized amide in the untreated by-product stream to form solid dimerized amide. Preferably, the precipitating is achieved by cooling at least a portion of the by-product stream. The process further comprises the step of separating the solid dimerized amide from the by-product stream to form a treated by-product stream. The treated by-product stream comprises a reduced amount, if any, of dimerized amide, e.g., solid dimerized amide.

In one embodiment, the present invention relates to an ammonium salt composition, e.g., a treated ammonium salt composition, comprising ammonium salt, e.g., ammonium sulfate, and a low amount, if any, of dimerized amide.

BRIEF DESCRIPTION OF THE DRAWINGS

The invention is described in detail below with reference to the appended drawings, wherein like numerals designate similar parts.

DETAILED DESCRIPTION OF THE INVENTION

Introduction

Figure 1:
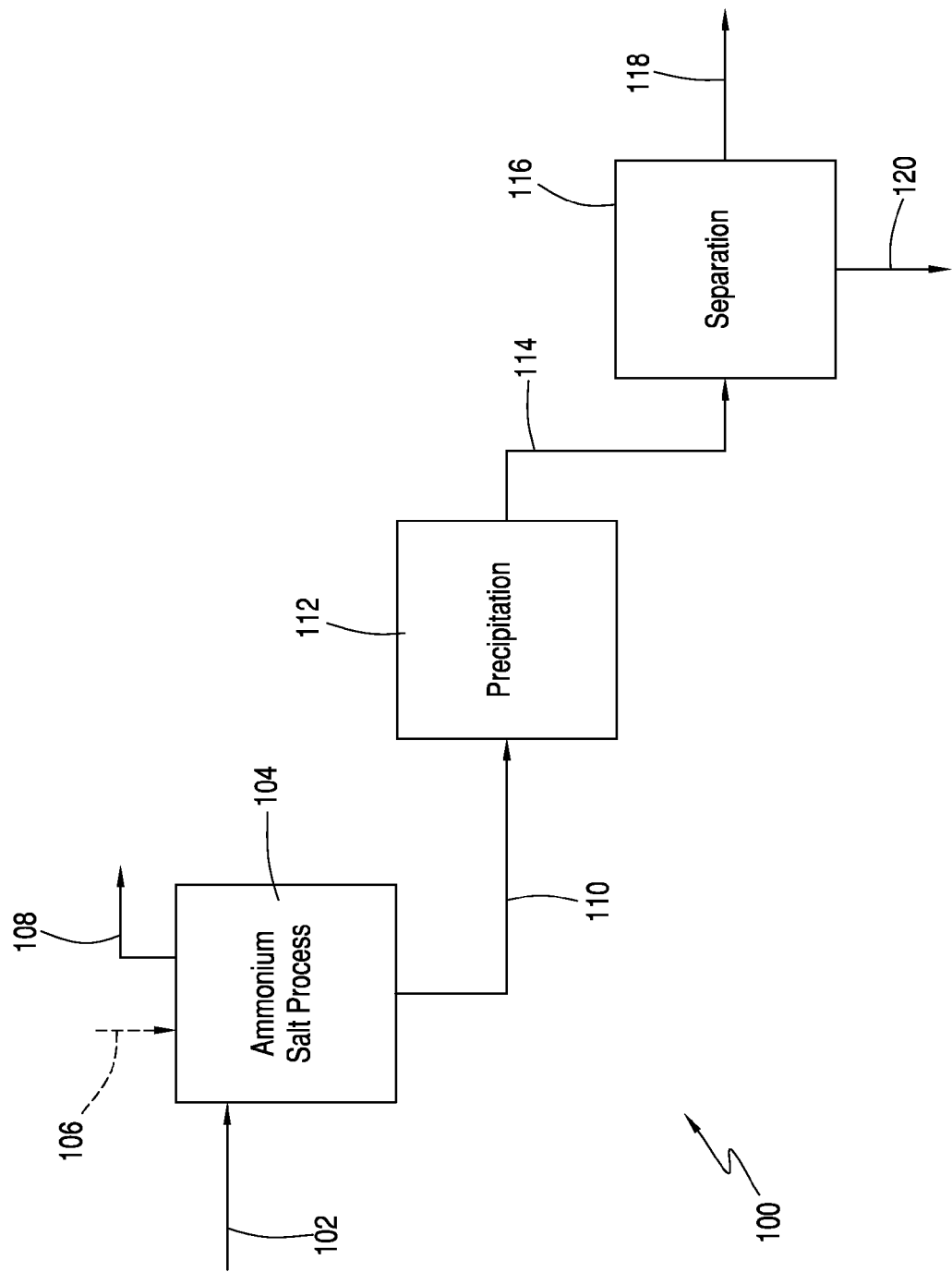
FIG. 1 is a process flowsheet of an ammonium sulfate production/purification process in accordance with an embodiment of the present invention.

Conventional processes may treat waste streams comprising acid, e.g., sulfuric acid, and amines, e.g., organic tertiary amines, with ammonia 1) to recover the organic tertiary amines; and 2) to produce ammonium sulfate, which is a by-product of the waste stream treatment. Thus, the contacting of the waste stream with ammonia yields a recovered amine stream and an ammonium salt-containing by-product stream. The untreated by-product stream is typically a liquid and may be considered to be an ammonium salt process stream, e.g., a process stream from an ammonium salt production process. As discussed above however, solids are known to form in the untreated by-product streams over time. These solids are known to cause processing and/or quality control problems, as discussed above.

It has now been discovered that the solids that form in the untreated by-product stream comprise organic by-products, e.g., crystallized dimerized amide. For example, the dimerized amide may comprise dimerized acetoacetamide. Other dimerized amides, such as those dimers that form in rearrangement reactions, are also contemplated. Without being bound by theory, it is believed that the dimerized amides are formed, along with the ammonium salt, as a by-product in the ammonia/sulfuric acid/amine reaction. Thus, the ammonium salt-containing by-product stream, as formed, comprises not only ammonium salt, but also dimerized amides. As the untreated by-product stream exits the reaction unit and proceeds to separation, collection, and/or shipment, the dimerized amides, over time, crystallize and precipitate out of the liquid. Surprisingly and unexpectedly, it has been found that at least a portion of the dimerized amide in the untreated by-product stream may be (intentionally) precipitated out of the by-product stream, e.g., prior to separation. In one embodiment, the precipitation step is performed substantially immediately after the formation of the by-product stream, e.g., after the reaction/separation of the sulfuric acid/tertiary amine waste stream. The precipitated dimerized amide may then be separated from the untreated by-product stream to yield a treated by-product stream. The treated by-product stream, beneficially, comprises lower amounts, if any, of the solid dimerized amide. The treated by-product stream may then be further separated and/or collected to yield the finished ammonium salt product. By performing the crystallization and separation in accordance with the present invention, the problems associated with the crystallized dimerized amide, e.g., crystallization in the final product and/or build-up on the walls of downstream process equipment, are reduced or avoided altogether.

Accordingly, in one embodiment, the present invention relates to a process for purifying a by-product stream, e.g., an ammonium salt-containing by-product stream. The process comprises the step of providing the untreated by-product stream, which comprises an ammonium salt, dimerized amide, e.g., liquid dimerized amide, and optionally water. The process further comprises the step of precipitating at least a portion of the dimerized amide in the untreated by-product stream to form solid dimerized amide. In one embodiment, the precipitation is performed prior to any additional separation, collection, and/or storage. In preferred embodiments, the precipitated solid dimerized amide forms a suspension with the remaining by-product stream, e.g., the solid dimerized amide is suspended in the liquid by-product solution. In one embodiment, the precipitating is achieved by cooling at least a portion of the by-product stream. Preferably, the cooling is achieved via application of a vacuum. In some embodiments, the use of vacuum-based cooling methods 1) allows the formation of the suspension; and 2) reduces or eliminates contact of the formed suspension with surfaces of the process equipment, e.g. the walls of the pipes and/or vessels, which beneficially reduces and/or eliminates the amount solid dimerized amide precipitation that collects on the process equipment. By keeping the precipitated dimerized amide in the suspension and away from the surfaces of the process equipment downstream of the reaction unit, the dimerized amide advantageously can be more effectively separated from the by-product stream.

Accordingly, the inventive process further comprises the step of separating the solid dimerized amide from the untreated by-product stream to form a treated by-product stream comprising a lower amount, if any, of dimerized amide. The lower amount of solid dimerized amide is lower than the amount of dimerized amide that would be present in a by-product stream in which the precipitating and separating steps are not performed. As a result of the inventive process, the treated by-product stream may comprise less than 1.0 wt % (solid) dimerized amide, e.g., less than 0.1 wt % or less than 0.01 wt %. In terms of ranges, the treated by-product stream may comprise from 0.0001 wt % to 1 wt % dimerized amide, e.g., from 0.001 wt % to 0.1 wt % or from 0.01 wt % to 0.1 wt %. As such, the treated by-product that is collected and/or delivered to an end user contains little or no solid precipitate. In preferred embodiments, the treated by-product stream exhibits substantially no dimerized amide precipitation once collected and/or stored. For example, the treated by-product stream may exhibit substantially no dimerized amide precipitation when stored at temperatures less than 20° C., e.g., less than 10° C. or less than 5° C., for more than 1 day, e.g., more than 2 days or more than 5 days.

In addition to the lower amounts of dimerized amide discussed above, the treated by-product stream may also comprise higher amounts of ammonium salt and/or higher percentages of ammonium salt. For example, in one embodiment, the treated-by product streams may comprise at least 35 wt % ammonium salt, e.g., at least 38 wt %, at least 40 wt % at least 42 wt %, at least 45 wt % or at least 55 wt %. In terms of ranges the treated by-product stream may comprise from 35 wt % to 75 wt % ammonium salt, e.g., from 35 wt % to 55 wt %, from 38 wt % to 50 wt %, from 40 wt % to 45 wt % or from 40 wt % to 42 wt %. In terms of upper limits, the treated by-product stream may comprise less than 75 wt %, e.g., less than 55 wt %, less than 45 wt %, or less than 42 wt %.

In one embodiment, the amount of (solid) dimerized amide in the treated by-product stream is at least 50% less than the amount of dimerized amide in the untreated by-product stream, e.g., at least 75% less or at least 99% less.

In addition to the dimerized amide and the ammonium salt, the untreated by-product stream and/or the treated by-product stream may further comprise organyl ammonium hydrogen sulfate, acetoacetamide, the organic cleavage products of acesulfame production and mixtures thereof In one embodiment, the separation of the solid dimerized amide from the remaining liquid by-products stream is achieved via filtration. The filtration process may vary widely and exemplary filtration separation schemes are discussed below.

In one embodiment, the process further comprises the step of disposing of the separated dimerized amide. As noted above, conventional processes do not separate the solid dimerized amide from the untreated by-product stream. Even if the solid dimerized amide precipitates naturally after being collected, e.g., during or after separation, the solid dimerized amide is not disposed of in conventional processes. Rather, the solid dimerized amide remains with the liquid by-product. The separation and disposal of the solid dimerized amide before collection, in accordance with the present invention, has not been contemplated.

In one embodiment, the inventive process further comprises the step of further purifying the treated by-product stream. In these embodiments, the treated by-product stream may be directed to an additional separation unit to remove from the by-product stream either 1) additional dimerized amide; or 2) other components of the by-product stream.

In one embodiment, the untreated by-product stream of the present invention results from the contacting of sulfuric acid and ammonia. For example, the untreated by-product stream may be formed when a sulfuric acid-containing waste stream from an acesulfame potassium production process is contacted with ammonia. Preferably, the contacting is performed via reaction and/or reactive distillation, wherein the ammonia is fed to a reactor or a reactive distillation column. The contacting of the sulfuric acid with the ammonia yields a by-product stream comprising, inter alia, the ammonium salt, e.g., ammonium sulfate, and dimerized amide.

In one embodiment, the untreated by-product stream comprises at least 35 wt % ammonium salt, e.g., at least 38 wt %, at least 40 wt % at least 42 wt %, at least 45 wt % or at least 55 wt %. In terms of ranges the untreated by-product stream may comprise from 35 wt % to 99 wt % ammonium salt, e.g., from 35 wt % to 75 wt %, from 35 wt % to 55 wt %, from 38 wt % to 50 wt %, from 40 wt % to 45 wt % or from 40 wt % to 42 wt %. In terms of upper limits, the untreated by-product stream may comprise less than 99 wt % ammonium salt, e.g., less than 75 wt % less than 55 wt %, less than 45 wt %, or less than 42 wt %. Preferably, the ammonium salt is ammonium sulfate. The ammonium salt, however, may vary based on the composition of the waste stream that may be separated to yield the by-product stream. For example, if phosphoric acid were used to form the waste stream, the resultant ammonium salt may be ammonium phosphate.

The untreated by-product stream comprises a significant portion of dimerized amide. In one embodiment, the untreated by-product stream comprises at least 0.1 wt % dimerized amide, e.g., at least 1 wt % or at least 2.5 wt %. In terms of ranges the untreated by-product stream may comprise from 0.1 wt % to 10 wt % dimerized amide, e.g., from 1 wt % to 10 wt % or from 1 wt % to 2.5 wt %. In terms of upper limits, the untreated by-product stream may comprise less than 10 wt % dimerized amide, e.g., less than 5 wt % or less than 2.5 wt %.

In one embodiment, the invention is to a process for producing a treated ammonium salt stream. The process comprises the step of contacting sulfuric acid and ammonia to form a crude (untreated) by-product stream and an amine product stream. The untreated by-product stream comprises ammonium salt and aqueous dimerized amide and the amine product stream comprises triethylamine. Preferably, the sulfuric acid is provided as a component of an acesulfame potassium process stream, which may optionally further comprise triethylamine. The process further comprises the steps of cooling the untreated crude product stream to precipitate at least a portion of the dimerized amide and separating at least a portion of the precipitated amides from the crude product stream to form a treated by-product stream comprising a low amount of solid dimerized amide. The combination of the precipitation and the separation surprisingly provides for the treated by-product stream that contains little, if any, solid dimerized amide.

In one embodiment, the inventive process may be characterized in terms of the solubilities of the components of the by-product stream. For example, the by-product stream may be processed such that the ammonium salt solubility limit in the by-product stream is greater than a dimerized amide solubility limit in the by-product stream. As a result, the dimerized amide precipitates out of the by-product stream before the ammonium salt. Once the precipitation occurs, the resultant composition may be separated, e.g., filtered, as discussed above. Preferably, the process is achieved via cooling the by-product stream.

Formation of By-Product Stream

As noted above, the present invention relates to the purification of a waste stream comprising acid(s) and amine(s) and/or precursors thereof. FIG. 1 is an overview of exemplary waste stream purification process 100. Waste stream 102 is directed to ammonium salt production unit 104. Waste stream 102 comprises acid, e.g., sulfuric acid, and amine, e.g., organic tertiary amine. In addition to producing ammonium salt, ammonium salt production unit 104 may also facilitate the separation and/or recovery of at least a portion of the amines from the waste stream. In one embodiment, in ammonium salt production unit 104, sulfuric acid in waste stream 102 is reacted with a basic compound, e.g., ammonia, to form a first amount of ammonium sulfate. The basic compound may be fed via optional feed line 106. Preferably, an excess of ammonia is utilized to maintain a pH value favorable for the formation of the desired products.

Amine product stream 108 exits ammonium salt production unit 104 and comprises the separated amines. The separated amines in amine product stream 108 may then be collected, re-used, and/or recycled. By-product stream 110 also exits ammonium salt production unit 104. By-product stream 110 comprises ammonium salt, dimerized amide, and optionally water. By-product stream 110 may be further processed.

As shown in FIG. 1, untreated by-product stream 110 is directed to precipitation zone 112. Precipitation zone 112 precipitates dimerized amide from untreated by-product stream 110, thus forming a suspension comprising the liquid portion of by-product stream 110 and the solid dimerized amide. By precipitating the dimerized amide from untreated by-product stream 110 before any subsequent processing, the problems associated with the downstream precipitation of the dimerized amide are significantly reduced and/or eliminated. The suspension is directed via line 114 to separation zone 116.

Separation zone 116 separates the solid dimerized amide from the remaining liquid by-product stream. Separation yields treated by-product stream 118 and solid dimerized amide stream 120. The composition of treated by-product stream 118 is discussed above. Solid dimerized amide stream 120 comprises primarily solid dimerized amide. In one embodiment, solid dimerized amide stream 120 may further comprise precipitated ammonium sulfate and/or organic cleavage products of acesulfame production.

In one embodiment, the tertiary amines are those comprising up to 20 carbon atoms per nitrogen atom, e.g., up to 12 carbon atoms. Examples of the amines that can be recovered from the process sulfuric acid stream are those selected from the group comprising trimethylamine, triethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine and triisopropylentriamine. Preferably, the tertiary amine comprises triethylamine.

The ammonia that can be reacted with waste stream 102, in some embodiments, may be used in gaseous or liquid form. In one embodiment, the partial pressure of the ammonia ranges 0.01 MPa to 30 MPa e.g., from 0.1 MPa to 10 MPa, and is limited only by the compressive strength of the equipment that is used. The ammonia may be used neat or as a mixture with other gases. The ammonia, in one embodiment, may be used as a solution in other solvents, preferably as an aqueous solution, and the aqueous solution may be obtained commercially or may be produced directly from the reaction by introducing gaseous or liquid ammonia in water. The heat of solution that is generated may either be removed or retained by transferring the heated solution to the following reaction step. To avoid the exhalation of ammonia, it is preferred to work at elevated pressure, e.g. a pressure greater than 0.1 MPa, e.g., greater than 1 MPa. In a preferred embodiment, to recover organic tertiary amines from the sulfuric acid stream, ammonia in gaseous or dissolved form may brought to the reaction with the sulfuric acid stream comprising the organic tertiary amines. Preferably, the ammonia is mixed with the sulfuric acid in an amount sufficient to obtain a pH greater than 9.5, e.g., greater than 10 or greater than 10.5. According to a preferred embodiment, the pH in the sulfuric acid-ammonia reaction ranges 9.8 to 12, e.g., from 10 to 11.5. In one embodiment, the ammonia is added to the sulfuric acid in an amount sufficient to obtain these ranges.

Suitable waste streams preferably contain from 0.1 wt % to 100 wt % of tertiary amines (optionally in the precursor form of the respective organyl ammonium hydrogen sulfate), e.g., from 1 wt % to 75 wt % or from 10 wt % to 50 wt %. Solutions may also contain free sulfuric acid and water. In one embodiment the process stream for example, comprises 35 wt % triethylammonium hydrogen sulfate, 45 wt % sulfuric acid, 16 wt % water, and minor amounts of organic components.

The reaction of the ammonia and the sulfuric acid, as discussed above, yields amine product stream 108, which comprises water, tertiary amine, ammonia, e.g., unreacted ammonia, and some ammonium salt, e.g., ammonium sulfate. Amine product stream 108 may be further processed (not shown). As one example of further processing, the tertiary amines may be separated and recovered. As another example, the unreacted ammonia may be separated and reacted with additional sulfuric acid to form additional ammonium sulfate.

Precipitation and Separation

As discussed above, ammonium sulfate production unit 104 forms ammonium sulfate as product. Ammonium sulfate solution provides a quickly recoverable, easily dosable, valuable nitrogen fertilizer. The ammonium sulfate content of by-product stream 110 may be controlled by adjusting 1) the water content of the reactant sulfuric acid, 2) the addition of water before, during or after the reaction and/or 3) distillation of water taking into account the solubility limit of ammonium sulfate in water.

Figure 2:
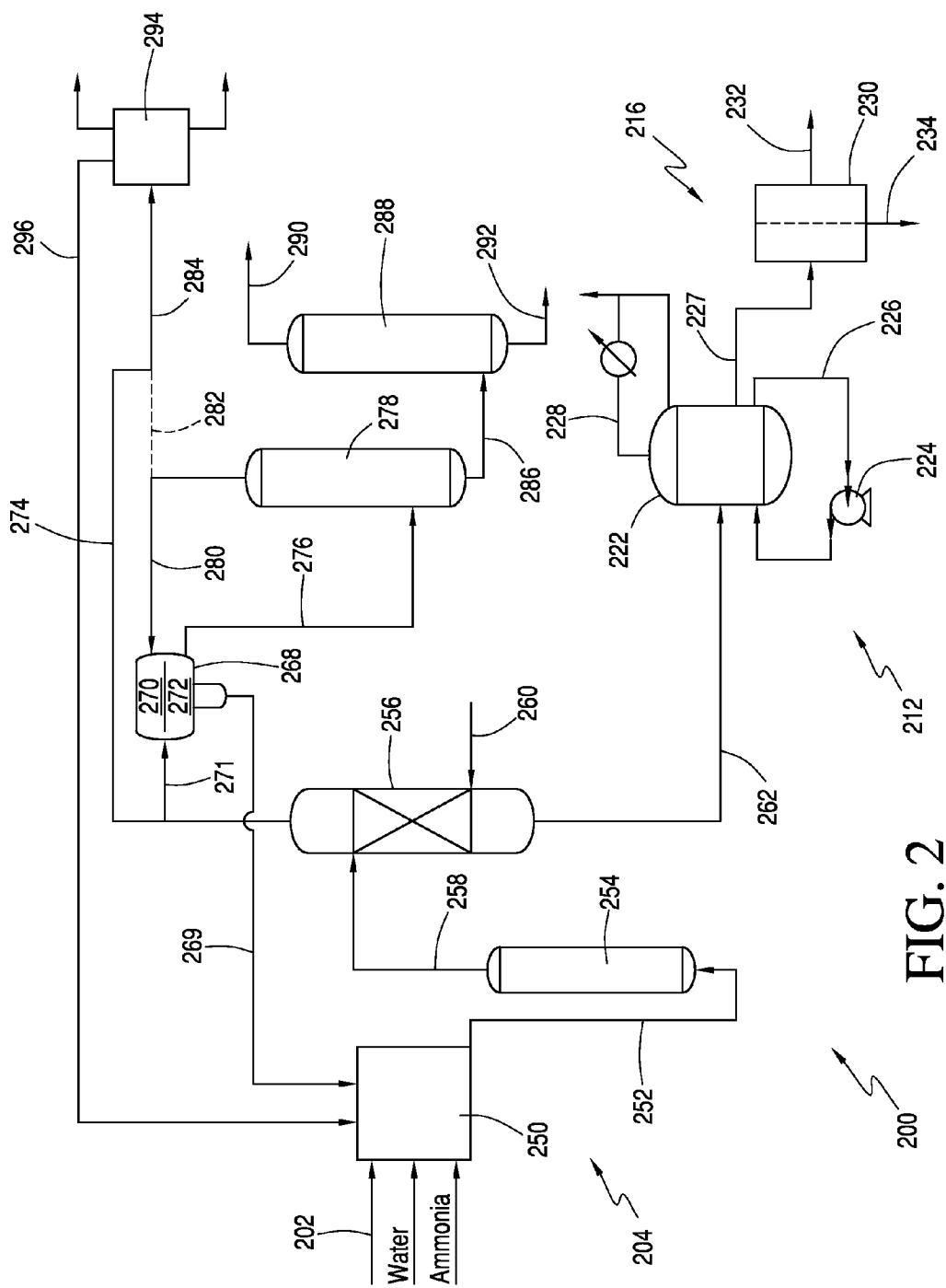
FIG. 2 is a schematic diagram of an ammonium sulfate production/purification process in accordance with an embodiment of the present invention.

FIG. 2 shows exemplary ammonium salt production process 200, which is in accordance with the present invention. Waste stream 202 comprises sulfuric acid and at least one tertiary amine (optionally in the form of the respective organyl ammonium hydrogen sulfate) and water. In a preferred embodiment, waste stream 202 is a waste stream from an acesulfame potassium production process, e.g., at least a portion of an aqueous sulfuric acid phase from an acesulfame potassium production process. Exemplary ranges for some of the components of waste stream 202 are shown in Table 1.

TABLE 1

| PROCESS STREAM COMPOSITION | | | |
|---|---|---|---|
| | Conc. (mol %) | Conc. (mol %) | Conc. (mol %) |
| Sulfuric Acid | 1 to 99 | 30 to 65 | 35 to 55 |
| Trialkylammonium Hydrogen Sulfate | 1 to 75 | 25 to 45 | 30 to 40 |
| Water | 1 to 99 | 5 to 50 | 10 to 25 |
| Organics | Less than 1 | Less than 0.5 | Less than 0.1 |

As shown in FIG. 2, waste stream 202 is directed to ammonium salt production unit 204. In one embodiment, ammonium salt production unit 204 comprises pre-reaction zone 250, reactor 254, and reactive distillation column 256. Pre-reaction zone 250 receives waste stream 202 as well as a water stream and an ammonia stream. Pre-reaction zone 250 prepares the reactants, e.g., sulfuric acid, water, and ammonia, for separation of the tertiary amines and/or conversion of sulfuric acid to ammonium sulfate. In one embodiment (not completely illustrated in FIG. 2), in pre-reaction zone 250, ammonia, e.g., gaseous ammonia, is fed to a first plug flow reactor, where the ammonia is diluted with water. The water may be provided to the first plug flow reactor from a water reservoir. The aqueous ammonia solution, thus formed, exits the first plug flow reactor and is conveyed to a second plug flow reactor, where the ammonia solution contacts the acesulfame potassium waste stream. The waste stream fed to the second plug flow reactor may be fed from a waste stream reservoir. The acesulfame potassium waste stream/ammonia product stream exits the second plug flow reactor, thus exiting pre-reaction zone 250, and is directed via line 252 to reactor 254.

In reactor 254 sulfuric acid from the waste stream contacts, e.g., reacts with, ammonia to form ammonium sulfate. In some embodiments, at least 50% of the sulfuric acid in process stream 100 is converted to ammonium sulfate in reactor 106, e.g., at least 90% or at least 95%. Reactor 254 preferably yields a crude stream comprising ammonium sulfate, triethylammonium sulfate, triethylamine, water, and unreacted ammonia. Reactor 254 is preferably a plug flow reactor, but other suitable reactor types, such as a stirred tank reactor or other tube-style reactors, may be employed as well. The reaction in reactor 254 is, in one embodiment, conducted under an elevated pressure, for example at a pressure ranging from 2 to 12 bar, e.g., from 7 to 10 bar, and at temperatures ranging from 95° C. to 140° C., e.g., from 100° C. to 126° C. or from 110° C. to 130° C.

In preferred embodiments, this reaction is carried out under basic conditions, e.g., the reaction is maintained at a high pH. In one embodiment, the pH of the reaction mixture is maintained at a level at least 8, at least 9, at least 9.5 or at least 10. In terms of ranges, the pH of the reaction mixture may be maintained at a level ranging from 8 to 12, e.g., from 9 to 12, or from 10 to 11.5. In one embodiment, the high pH level is maintained by mixing ammonia with the waste sulfuric acid. Maintaining the pH at these levels provides for 1) efficient tertiary amine separation, 2) efficient sulfuric acid conversion, and 3) a product ammonium sulfate having a low total organic content, e.g., less that 1 wt % organic content or less than 0.5 wt % organic carbon content, based on the total amount of dried ammonium sulfate obtained.

In a preferred embodiment, water is added to the reaction mixture to avoid precipitation of ammonium sulfate, which occurs as the solubility limit is exceeded during or after the reaction. This precipitation may be avoided, for example, by diluting process stream 202 with water prior to introduction into reactor 254, or by adding water to reactor 254, or by diluting the reaction solution. The water may be provided as a recycled aqueous phase from a decanter, see below.

Although FIG. 2 shows one reactor, there may be multiple reactors for reacting the process stream and aqueous ammonia stream.

In a preferred embodiment, the sulfuric acid and the ammonia are reacted in reactor 254 and are further reacted and/or separated in separation unit, e.g., reactive distillation column, 256. In this case, the reaction mixture exits reactor 254 and is directed via line 258 to separation unit 256. Separation unit 256 is preferably a distillation column, e.g., a reactive distillation column, however, other suitable separation units, such as extractors and phase separators may be employed. Distillation is especially advantageous in cases where the amines in the product stream have a low boiling point, are highly soluble in water, and/or form an azeotrope with water. Although FIG. 2 shows a single separation unit, multiple separation units may also be employed. Distillation may be performed directly from the reaction vessel or in a two stage apparatus.

In one embodiment, separation unit 256 is operated under basic conditions. Preferably, these basic conditions are achieved by adding ammonia, e.g., via ammonia feed 260. In one embodiment, the pH of the distillation fluid in separation unit 256 is maintained at a level at least 8, at least 9, at least 9.5 or at least 10. In terms of ranges, the pH of the distillation fluid may be maintained at a level ranging from 8 to 12, e.g., from 9 to 12, or from 10 to 11.5. Also, ammonia may be added to react with sulfuric acid present in separation unit 256 to form ammonium sulfate. Ammonia is added in a molar excess in separation unit, such that the molar ratio of ammonia to sulfuric acid is greater than 1.2:1, e.g., greater than 1.5:1. The excess molar ratio is needed to ensure complete reaction of the sulfuric acid.

Preferably, the ammonia is added to the distillation column counter to the flow the reaction mixture. In one embodiment, during the distillation, the sulfuric acid-ammonia reaction mixture is continuously fed to the upper part of a distillation column and the ammonia is continuously fed at the lower part or the middle part of the distillation column. The position of the ammonia feed may be used to control the pH of the reaction mixture being separated. The amount of ammonia and, consequently, the adjusted pH value, influence the capacity of the column with respect to separation of the tertiary amines from the aqueous ammonium sulfate solution. The closer the ammonia feed is to the bottom of the distillation column, the higher the pH of the reaction mixture in the bottom of the column.

Also, the position of the ammonia feed to the distillation column also may influence the pH of the aqueous solution comprising ammonium sulfate, which exits the bottom of the separation unit, e.g., distillation column. In a preferred embodiment, the ammonia feed is positioned on the distillation column such that the aqueous ammonium sulfate solution, which is essentially free of the organic tertiary amine, in the lower part of the column has a pH ranging from 5 to 7, e.g., from 5.5 to 6.5.

In one embodiment, the inventive process further comprises the step of dewatering the recovered tertiary amine, which can optionally be followed by further distillation of the dewatered amine. Preferably, the organic tertiary amine, e.g., triethylamine, is recovered in a yield of at least 99.0%, e.g., at least 99.5% or at least 99.9%.

In one embodiment (not shown), the organic tertiary amine may be separated from the reaction mixture by extraction with an organic liquid, preferably a liquid hydrocarbon. In one preferred embodiment, the organic liquid comprises an aliphatic liquid hydrocarbon comprising at least 8 carbon atoms, e.g., at least eight carbon atoms, most preferably being octane. The methods for the separation of the organic amines may be applied individually or in combination.

Separation unit 256 yields an untreated by-product stream comprising ammonium salt, e.g., ammonium sulfate, dimerized amide, and water, which exits separation unit 256 via line 262. This untreated by-product stream may be directed to precipitation zone 212. The temperature of the by-product stream as it exits separation unit 256 may be at least 95° C., e.g., at least 100° C., or at least 105° C. In terms of ranges, the temperature of the by-product stream as it exits separation unit 256 may range from 95° C. to 120° C., e.g., from 100° C. to 115° C., from 105° C. to 110° C., or from 107° C. to 108° C. In terms of lower limits, the temperature of the by-product stream as it exits separation unit 256 may be less than 120° C., e.g., less than 115° C., or less than 110° C. In one embodiment, the untreated by-product stream has a pH ranging from 5.6 to 6.2, e.g., from 5.7 to 5.9. In one embodiment, the untreated by-product stream has a density ranging from 1150 kg/m$^3$ to 1250 kg/m$^3$, e.g., from 1175 kg/m$^3$ to 1225 kg/m$^3$ or from 1185 kg/m$^3$ to 1195 kg/m$^3$.

Precipitation zone 212 precipitates dimerized amide from the by-product stream in line 262, thus forming a suspension comprising the liquid portion of by-product stream 262 and the solid dimerized amide. As shown in FIG. 2, precipitation zone 212 may comprise a single unit, e.g., precipitation vessel 222. Precipitation vessel 222 may comprise a stirrer or an agitator (not shown). Although FIG. 2 shows only one exemplary precipitation unit, the present invention contemplates the used of one or more, e.g., two or more, suitable precipitation units. Other exemplary precipitation units include crystallizers, heat exchangers, chillers, evaporators, cooling traps, and combinations thereof In one embodiment, the untreated by-product stream in line 262 is conveyed directly to precipitation vessel 222, e.g., without cooling. In preferred embodiments, precipitation vessel 222 utilizes a vacuum to precipitate the dimerized amide from the by-product stream. Preferably, one or more ring pumps 224 are employed to apply a vacuum to precipitation vessel 222. The reduction in pressure achieved by the vacuum pump(s) reduces the temperature of the by-product stream that has gathered in precipitation vessel 222. It has now been discovered that the use of vacuum-based cooling methods beneficially provides for the formation of the suspension. By keeping the precipitated dimerized amide in the suspension, the dimerized amide is kept away from the surfaces of the process equipment, e.g. the walls of the pipes and/or vessels, which beneficially reduces and/or eliminates the amount solid dimerized amide precipitation that collects on the process equipment. In addition, the dimerized amide, when in suspension, beneficially can be more effectively separated from the by-product stream.

In one embodiment, the temperature of the by-product stream in precipitation vessel 222 may be at least 20° C., e.g., at least 30° C., or at least 35° C. In terms of ranges, the temperature of the by-product stream in precipitation vessel 222 may range from 20° C. to 65° C., e.g., from 30° C. to 45° C. or from 30° C. to 40° C. In terms of upper limits, the temperature of the by-product stream in precipitation vessel 222 may be less than 65° C., e.g., less than 45° C., or less than 40° C. In one embodiment, the temperature of the by-product stream in precipitation vessel 222 is at least 10° C. less than the temperature of the by-product stream as it exits ammonium salt production vessel 204, e.g., at least 25° C. less than, at least 50° C. less than, or at least 75° C. less than. The temperature of the by-product stream in precipitation vessel 222 ranges from 1220 kg/m$^3$ to 1240 kg/m$^3$, e.g., from 1225 kg/m$^3$ to 1235 kg/m$^3$ or from 1228 kg/m$^3$ to 1231 kg/m$^3$.

In one embodiment, the suspension may be recycled, e.g., via line 226, through precipitation vessel 222 until the desired temperature is reached. Also, as shown in FIG. 2, water may be drawn from precipitation vessel 222 via line 228. The withdrawn water may be removed from the process or may be recycled to precipitation vessel 222 so as to maintain a desired concentration of ammonium sulfate in the suspension.

The suspension exits precipitation zone 212 and is directed to separation zone 216 via line 227. Separation zone 216 separates the solid dimerized amide from the liquid portion of the by-product stream. Separation zone 216 may employ one or more separation units to perform the separation. As a result, separation zone 216 yields a treated by-product stream in line 232 and a stream comprising the solid dimerized amide in line 234. The dimerized amide, as formed, may be collected and disposed, e.g., incinerated. The composition of the treated by-product stream is discussed above. The treated by-product stream comprises primarily ammonium salt and may be collected, used, and/or sold.

The unit(s) of the separation zone may vary widely. Exemplary separation units include filtration units, sedimentation units, cyclones, and combinations thereof. As shown in FIG. 2, separation zone 216 may comprise filtration unit 230. In a preferred embodiment, filtration unit 230 comprises two parallel filters. These filters can be operated separately so as to maintain continuous operation. As an example, filter bags and/or filter plates may be used to achieve the separation of the dimerized amide and the remainder of the by-product stream.

Returning to separation unit 256, separation unit 256 also yields a distillate comprising triethylamine, water, unreacted ammonia, methylene dichloride, and acetone. In one embodiment, the distillate comprises a triethylamine-water azeotrope. The distillate from separation unit 256, in one embodiment, is condensed to yield a liquid stream and a vapor stream. The liquid stream is conveyed via line 271 to phase separation unit 268, which is preferably a decanter. Phase separation unit 268 separates the liquid phase of the distillate into upper liquid organic phase 270, which comprises triethylamine, and lower liquid aqueous phase 272, which comprises water and may be recycled via line 269 to pre reaction zone 250. A vapor stream, e.g., at least a portion of an off gas, comprising methylene dichloride and ammonia, e.g., a preliminary amount of ammonia, exits separation unit 256 via line 274 and, once separated from the liquid phase, is directed to further processing. In one embodiment, the off gas further comprises acetone. In one embodiment, the off gas comprises from 25 mol % to 99.9 mol % ammonia, based on the total weight of the off gas, e.g., from 50 mol % to 99 mol % or from 75 mol % to 98 mol %. In terms of upper limits, the off gas may comprise less than 99.9 mol % ammonia, e.g., less than 99 mol % or less than 98 mol %. It is appreciated that the off gas may contain a significant amount of ammonia. In terms of lower limits, the off gas may comprise at least 50 mol % ammonia, e.g., at least 75 mol % or at least 90 mol %.

Upper liquid organic phase 270 is directed via line 276 to column 278, which preferably is a dewatering column. Column 278 separates upper liquid organic phase 270 into a distillate comprising a water/triethylamine azeotrope and optionally ammonia and a residue comprising triethylamine. At least a portion of the water/triethylamine azeotrope is recycled to phase separation unit 268 via line 280. In one embodiment, at least a portion of the ammonia in the distillate of column 278 is combined with line 274 via optional line 282 to form combined ammonia feed line 284. The triethylamine-containing residue is directed via line 286 to column 288, which is preferably a distillation column. Column 288 separates the contents of line 286 into a triethylamine distillate and a residue comprising high boiling point organic compounds. The distillate from column 288 comprises purified triethylamine is withdrawn via line 290 and is optionally recycled to an acesulfame potassium production process (not shown). The residue exits column 288 via line 292 and is disposed accordingly.

The off gas in line 274 exiting phase separation unit 268 is optionally combined with ammonia in line 282 and directed to further processing, e.g., ammonium conversion. Ammonia conversion unit 294 receives the ammonia in line 284. In one embodiment, ammonia conversion unit 294 comprises a washing column or a reactive distillation column. In ammonia conversion unit 294, the ammonia-containing off gas is contacted with sulfuric acid to form ammonia salts, e.g., ammonium sulfate. The ammonium sulfate exits ammonia conversion unit 294 via line 296. Preferably, the ammonium sulfate-containing residue from ammonia conversion unit 294 is recycled to separation unit 256 (via pre-reaction zone 250), where the additional ammonium sulfate may be recovered in the residue of separation unit 256 (recycle. Water may also be provided to ammonia conversion unit 294. Unreacted ammonia, if any, exits ammonia conversion unit 294 as an exhaust vent.

In one embodiment, the ammonia conversion unit may be a column. Other suitable unit(s), however, may also be employed, e.g., a reactor, a scrubber, a spray tower, or a tube-style reactor. Methods of contacting the reactants are well known in the art and it is well within the skill of the art to utilize an appropriate unit to perform the contacting step.

In preferred embodiments, the acid used to contact the off gas is sulfuric acid, and the resultant ammonium salt comprises ammonium sulfate. However, in other embodiments, acids other than sulfuric acid may be employed. In such cases, the resultant ammonium salt will correspond to the acid that is employed. For example, if phosphoric acid were utilized, the resultant ammonium salt would comprise ammonium phosphate.

The ammonium sulfate production process of the present invention may be used with any suitable process stream comprising a suitable acid. In a preferred embodiment, the process stream comprises an acesulfame potassium waste stream that results from an acesulfame potassium production process. One exemplary process reacts sulfamic acid and/or a salt thereof and diketene may be reacted to form an acetoamide salt, e.g., acetoacetamide-N-sulfonate triethylammonium salt. In preferred embodiments, the acetoamide salt serves as an intermediate in the formation of the cyclized acesulfame-H. The reaction product containing the acetoacetamide salt is then cyclized, preferably utilizing sulfur trioxide. The cyclized product is then hydrolized to form acesulfame-H, the acid form of acesulfame-K. The hydrolysis reaction is preferably carried out via addition of water (or ice) and optionally aqueous sulfuric acid.

The hydrolysis reaction yields a multiple phase mixture, which is directed to a phase separation unit, e.g., decanter. The decanter separates the multiple phase mixture into an organic phase, an aqueous phase (sulfuric acid phase), and optionally a solid precipitate phase. The aqueous phase comprises sulfuric acid and at least one tertiary amine. As such, this aqueous phase may serve as a process stream for use in embodiments of the present invention.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for purifying a by-product stream, the process comprising the steps of:
   (a) providing a by-product stream comprising an ammonium salt, dimerized amide, and optionally water;
   (b) precipitating at least a portion of the dimerized amide in the by-product stream to form solid dimerized amide; and
   (c) separating the solid dimerized amide from the by-product stream to form a treated by-product stream comprising less than 1 wt. % dimerized amide.

2. The process of claim 1, wherein step (b) comprises the step of cooling at least a portion of the by-product stream.

3. The process of claim 2, wherein the step of cooling occurs under a vacuum.

4. The process of claim 3, wherein step (c) comprises: separating the solid dimerized amide from the by-product stream via filtration.

5. The process of claim 1, wherein step (c) comprises: separating the solid dimerized amide from the by-product stream via filtration.

6. The process of claim 1, wherein the solid dimerized amide and the by-product stream form a suspension.

7. The process of claim 1, wherein step (c) comprises: separating the suspension via filtration.

8. The process of claim 1, further comprising the step of: disposing of the separated solid dimerized amide.

9. The process of claim 1, further comprising the step of: further purifying the treated by-product stream to recover ammonium salt therefrom.

10. The process of claim 9, wherein step (b) is performed before the further purification.

11. The process of claim 1, wherein step (b) is performed substantially immediately after formation of the by-product stream.

12. The process of claim 1, wherein the treated by-product stream exhibits substantially no dimerized amide precipitation after storage at less than 20° C. for more than 1 day.

13. The process of claim 1, wherein step (a) comprises: contacting sulfuric acid and ammonia to form the by-product stream.

14. The process of claim 13, wherein the contacting is performed via reactive distillation.

15. The process of claim 1, wherein the by-product stream comprises:
from 1 wt % to 75 wt % ammonium salt; and
from 0.1 wt % to 10 wt % dimerized amide.

16. The process of claim 1, wherein the treated by-product stream comprises:
from 35 wt % to 99 wt % ammonium salt; and
from 0.0001 wt % to 1 wt % dimerized amide.

17. The process of claim 1, wherein the ammonium salt comprises ammonium sulfate.

18. The process of claim 1, wherein the dimerized amide comprises dimerized acetoacetamide.

19. A process for producing a treated ammonium salt stream, the process comprising the steps of:
(a) contacting sulfuric acid and ammonia to form a crude by-product stream comprising ammonium salt and aqueous dimerized amide and an amine product stream comprising triethylamine;
(b) cooling the crude by-product stream to precipitate at least a portion of the dimerized amide;
(c) separating at least a portion of the precipitated amides from the crude by-product stream to form a treated by-product stream comprising less than 1 wt. % solid dimerized amide.

20. The process of claim 19, wherein step (b) occurs under a vacuum.

* * * * *